US009011312B2

(12) United States Patent
Bourque

(10) Patent No.: US 9,011,312 B2
(45) Date of Patent: *Apr. 21, 2015

(54) GENERATING ARTIFICIAL PULSE

(71) Applicant: Thoratec Corporation, Pleasanton, CA (US)

(72) Inventor: Kevin Bourque, Reading, MA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,044

(22) Filed: Jun. 25, 2013

(65) Prior Publication Data

US 2013/0289336 A1    Oct. 31, 2013

Related U.S. Application Data

(63) Continuation of application No. 13/241,831, filed on Sep. 23, 2011, now Pat. No. 8,506,471.

(60) Provisional application No. 61/386,018, filed on Sep. 24, 2010.

(51) Int. Cl.
*A61N 1/362* (2006.01)
*A61N 1/10* (2006.01)
(Continued)

(52) U.S. Cl.
CPC .............. *A61M 1/122* (2014.02); *A61M 1/101* (2013.01); *A61M 1/1086* (2013.01); *A61M 2205/3365* (2013.01)

(58) Field of Classification Search
None
See application file for complete search history.

(56) References Cited

U.S. PATENT DOCUMENTS

| 4,296,500 | A | 10/1981 | Monties et al. |
| 4,957,504 | A | 9/1990 | Chardack |
| 6,066,086 | A | 5/2000 | Antaki et al. |

(Continued)

FOREIGN PATENT DOCUMENTS

| EP | 2298375 A1 | 3/2011 |
| GB | 2152241 A | 7/1985 |

(Continued)

OTHER PUBLICATIONS

"Speed modulation of the continuous-flow total artificial heart to simulate a physiologic arterial pressure waveform" by Akira Shiose et al. in ASAIO Journal Sep./Oct. 2010—vol. 56—Issue 5—pp. 403-409. (published online Sep. 7, 2010).

(Continued)

*Primary Examiner* — Brian T Gedeon
(74) *Attorney, Agent, or Firm* — Kilpatrick Townsend and Stockton LLP

(57) ABSTRACT

In order to produce a pulsatile blood flow pattern that includes time periods of relatively high blood flow rates and time periods of relatively low blood flow rates, the operating speed of a blood pump can be selectively controlled to produce an operating speed pattern that includes time periods of relatively high rotation speeds and periods of relatively low rotation speeds. For example, the blood pump is rotated at a first speed for a first period of time. The speed of the blood pump is then decreased from the first speed to a second speed and is operated at the second speed for a second amount of time. The speed of the blood pump is then decreased to a third speed for a third amount of time. If desired, the operating speed pattern can be repeated to continue the pulsatile blood flow pattern.

38 Claims, 4 Drawing Sheets

(51) Int. Cl.
*A61M 1/12* (2006.01)
*A61M 1/10* (2006.01)

(56) References Cited

U.S. PATENT DOCUMENTS

| | | | |
|---|---|---|---|
| 6,293,901 B1 | 9/2001 | Prem | |
| 6,422,990 B1 | 7/2002 | Prem | |
| 6,547,753 B1 | 4/2003 | Plunkett et al. | |
| 6,623,420 B2 * | 9/2003 | Reich et al. | 600/17 |
| 6,969,345 B2 | 11/2005 | Jassawalla et al. | |
| 7,160,242 B2 | 1/2007 | Yanai | |
| 7,578,782 B2 | 8/2009 | Miles et al. | |
| 7,861,582 B2 | 1/2011 | Miyakoshi et al. | |
| 8,506,471 B2 | 8/2013 | Bourque | |
| 2003/0199727 A1 | 10/2003 | Burke et al. | |
| 2005/0071001 A1 | 3/2005 | Jarvik | |
| 2005/0131271 A1 | 6/2005 | Benkowski et al. | |
| 2007/0073393 A1 | 3/2007 | Kung et al. | |
| 2007/0083077 A1 | 4/2007 | Frazier | |
| 2009/0099406 A1 | 4/2009 | Salmonsen et al. | |
| 2009/0138080 A1 | 5/2009 | Siess et al. | |
| 2010/0152526 A1 | 6/2010 | Pacella et al. | |
| 2010/0222635 A1 | 9/2010 | Poirier | |
| 2011/0054239 A1 | 3/2011 | Sutton et al. | |
| 2011/0112354 A1 | 5/2011 | Nishimura et al. | |
| 2012/0078031 A1 | 3/2012 | Burke et al. | |

FOREIGN PATENT DOCUMENTS

| | | |
|---|---|---|
| JP | 2003/501180 A | 1/2003 |
| JP | 2009297174 A | 12/2009 |
| WO | 00/76822 A1 | 12/2000 |
| WO | WO0172352 A2 | 10/2001 |
| WO | WO 2005/051838 | 6/2005 |
| WO | WO2006133409 A2 | 12/2006 |
| WO | WO2009150893 A1 | 12/2009 |

OTHER PUBLICATIONS

"Flow Modulation Algorithms for Continuous Flow Left Ventricular Assist Devices to Increase Vascular Pulsatility: A Computer Simulation Study" by Mickey Ising, Sean Warren, Michael A. Sobieski, Mark S. Slaughter, Steven C. Koenig and Guruprasad A. Giridharan, Cardiovascular Engineering and Technology vol. 2, No. 2, 90-100, DOI: 10.1007/s13239-011-0042-x (Mar. 26, 2011).

Adam R. Travis et al, "Vascular pulsatility in patients with a pulsatile-or continuous-flow ventricular assist device," The Journal of Thoracis and Cardiovascular Surgery, vol. 133, No. 2, Feb. 2007, pp. 517-524.
Stijn Vandenberghe et al., "Hemodynamic Modes of Ventricular Assist with a Rotary Blood Pump: Continuous, Pulsatile, and Failure," ASAIO Journal 2005, vol. 51; pp. 711-718.
Kiyotaka Fukamachi et al., "An innovative, sensorless, pulsatile, continuous-flow total artificial heart: Device design and initial in vitro study," The Journal of Heart and Lung Transplantation, vol. 29, No. 1, Jan. 2010, pp. 13-20.
Hassan A. Khalil et al., "Induced pulsation of a continuous-flow total artificial heart in a mock circulatory system," The Journal of Heart and Lung Transplantation, vol. 29, No. 5, May 2010, pp. 568-573.
Yubing Shi et al., "Numerical Simulation of Cardiovascular Dynamics With Left Heart Failure and In-series Pulsatile Ventricular Assist Device," Artificial Organs, vol. 30, No. 12, 2006, pp. 929-948.
Yubing Shi et al., "Numerical Modeling of Hemodynamics with Pulsatile Impeller Pump Support," Annals of Biomedical Engineering, vol. 38, No. 8, Aug. 2010. (published online Mar. 16, 2010).
Authorized Officer Trudy Hinterwimmer, PCT Invitation to Pay Additional Fees for Application No. PCT/US2011/052897 mailed Dec. 13, 2011, 5 pages.
Authorized Officer Trudy Hinterwimmer, PCT Search Report and Written Opinion for Application No. PCT/US2011/052912 mailed Dec. 19, 2011, 13 pages.
Authorized Officer Philip Jones, PCT Search Report and Written Opinion for Application No. PCT/US2011/052897 mailed Feb. 1, 2012, 17 pages.
U.S. Notice of Allowance for U.S. Appl. No. 13/241,831 dated Apr. 2, 2013, 18 pages.
PCT International Preliminary Report on Patentability for International Application No. PCT/US2011/052897 dated Mar. 26, 2013, 12 pages.
PCT International Preliminary Report on Patentability for International Application No. PCT/US2011/052912 dated Mar. 26, 2013, 9 pages.
U.S. Notice of Allowance for U.S. Appl. No. 13/241,831 dated May 7, 2013, 10 pages.
English Translation and Notice of Reasons for Rejection for corresponding Japanese Application No. 2013-530346 mailed on Oct. 30, 2014, 8 pages.
Notice of Allowance for U.S. Appl. No. 14/261,817 mailed on Oct. 9, 2014, 9 pages.
Final Office Action for U.S. Appl. No. 13/242,248 mailed on Oct. 28, 2014, 17 pages.

* cited by examiner

GENERATING ARTIFICIAL PULSE

CROSS-REFERENCE TO RELATED APPLICATIONS

This application is a continuation (and claims the benefit of priority under 35 U.S.C. §120) of U.S. application Ser. No. 13/241,831, filed Sep. 23, 2011 (now U.S. Pat. No. 8,506,471), which claims priority to and the full benefit of U.S. Provisional Application Ser. No. 61/386,018, filed Sep. 24, 2010, and titled "Generating Artificial Pulse." The entire contents of both applications are incorporated herein by reference.

FIELD

This description relates to generating an artificial pulse.

BACKGROUND

Ventricular assist devices, known as VADs, are types of blood pumps used for both short-term and long-term applications where a patient's heart is incapable of providing adequate circulation. For example, a patient suffering from heart failure may use a VAD while the patient awaits a heart transplant. In another example, a patient may use a VAD while the patient recovers from heart surgery. Thus, a VAD can supplement a weak heart or can effectively replace the natural heart's function. VADs can be implanted in the patient's body and powered by an electrical power source outside the patient's body.

SUMMARY

In one general aspect, a continuous flow blood pump can be operated to provide pulsatile blood flow. The motor speed for the pump can be modulated in a repeating cycle that includes a sequence of two or more speed levels. Operation of the pump can produce pressure changes that imitate a rate of pressure change of a natural physiologic pulse.

In another general aspect, pumping blood in a pulsatile manner includes operating a blood pump at a first speed for a first period of time, reducing the speed of the blood pump from the first speed to a second speed, operating the blood pump at the second speed for a second period of time, reducing the speed of the blood pump from the second speed to a third speed, operating the blood pump at the third speed for a third period of time, and increasing the speed of the blood pump from the third speed to the first speed.

Implementations can include one or more of the following features. For example, increasing the speed of the blood pump from the third speed to the first speed includes increasing the speed of the blood pump from the third speed to a fourth speed, operating the blood pump at the fourth speed for a fourth period of time, and increasing the speed of the blood pump from the fourth speed to the first speed. The second period of time is longer than a sum of the first period of time and the third period of time. Operating the blood pump at the first speed, reducing the speed of the blood pump from the first speed to the second speed, operating the blood pump at the second speed, reducing the speed of the blood pump from the second speed to the third speed, operating the blood pump at the third speed, and increasing the speed of the blood pump from the third speed to the first speed comprise a cycle, and pumping blood in a pulsatile manner further includes repeating the cycle. The duration of the second period of time is greater than half of the duration of the cycle. Operating the blood pump at the second speed for the second period of time includes operating the blood pump to produce a blood flow rate that has a predetermined relationship relative to an average blood flow rate for the cycle. Operating the blood pump at the second speed for the second period of time includes operating the blood pump to produce a blood flow substantially the same as the average blood flow rate for the cycle.

One or more of reducing the speed of the blood pump from the first speed to a second speed, reducing the speed of the blood pump from the second speed to a third speed, and increasing the speed of the blood pump from the third speed to the first speed includes one or more of a step-wise reduction in speed and a curvilinear reduction in speed. Operating the blood pump at the second speed includes operating the blood pump at the second speed during at least a portion of a contraction of a ventricle of human heart that is in blood flow communication with the blood pump. Pumping blood in a pulsatile manner also includes determining, based on a relationship between a speed of the blood pump and a power consumption of the blood pump, a synchronization between operating the impeller at the second speed and contraction of a ventricle of a human heart that is in blood flow communication with the blood pump. A generated pulsatile blood flow includes a temporal rate of change of blood pressure that approximates a temporal rate of change of blood pressure of a physiologic pulse. One or more of reducing the speed of the blood pump from the first speed to a second speed, reducing the speed of the blood pump from the second speed to a third speed, and increasing the speed of the blood pump from the third speed to the first speed includes generating a drive signal at a first time to produce a corresponding change in operating speed at a desired time. The second period of time is greater than the first period of time.

In another general aspect, a blood pump controller includes a waveform generator to generate a waveform for operating a blood pump, and a drive waveform transmitter to supply the generated drive waveform to the blood pump. The generated waveform is configured to operate a blood pump at a first speed for a first period of time, reduce the speed of the blood pump from the first speed to a second speed, operate the blood pump at the second speed for a second period of time, reduce the speed of the blood pump from the second speed to a third speed, operate the blood pump at the third speed for a third period of time, and increase the speed of the blood pump from the third speed to the first speed.

Implementations can include one or more of the following features. For example, increasing the speed of the blood pump from the third speed to the first speed includes increasing the speed of the blood pump from the third speed to a fourth speed, operating the blood pump at the fourth speed for a fourth period of time, and increasing the speed of the blood pump from the fourth speed to the first speed. The second period of time is longer than a sum of the first period of time and the third period of time. Operating the blood pump at the first speed, reducing the speed of the blood pump from the first speed to the second speed, operating the blood pump at the second speed, reducing the speed of the blood pump from the second speed to the third speed, operating the blood pump at the third speed, and increasing the speed of the blood pump from the third speed to the first speed comprise a cycle, and wherein the generated waveform is configured to repeat the cycle. The duration of the second period of time is greater than half of the duration of the cycle. Operating the blood pump at the second speed for the second period of time includes operating the blood pump to produce a blood flow rate that has a predetermined relationship relative to an average blood flow rate for the cycle. Operating the blood pump at the second speed for the second period of time includes operating the blood pump to produce a blood flow substantially the same as the average blood flow rate for the cycle.

The generated waveform is configured to change the speed of the blood pump via one or more of a step-wise change in speed and a curvilinear change in speed. The generated waveform operates the blood pump at the second speed during a contraction of a ventricle of a human heart that is in blood flow communication with the blood pump. The blood pump controller further includes a processor configured to determine, based on a relationship between a speed of the blood pump and a power consumption of the blood pump, a synchronization between operating the blood pump at the second speed and a contraction of a ventricle of a human heart that is in blood flow communication with the blood pump. The generated waveform drives the blood pump to generate a temporal rate of change of blood pressure that approximates a temporal rate of change of blood pressure of a physiologic pulse. The generated waveform is further configured to produce a corresponding change in pump operating speed at a desired time. The second period of time is greater than the first period of time.

In another general aspect, producing a pulsatile blood flow having a relatively low pressure portion and a relatively high pressure portion and having a rate of pressure change that mimics a rate of pressure change of a natural physiologic pulse includes operating a continuous flow blood pump to produce a first blood flow rate through the continuous flow blood pump associated with the relatively low pressure portion of the pulsatile blood flow, operating the continuous flow blood pump to produce a second blood flow rate through the continuous flow blood pump associated with the relatively high pressure portion of the pulsatile blood flow, and controlling the continuous flow blood pump to increase a blood flow rate through the continuous flow blood pump from the first flow rate to the second flow rate to produce the rate of pressure change that mimics the rate of pressure change of the natural physiologic pulse.

Implementations can include one or more of the following features. For example, operating the continuous blood flow pump to produce the second blood flow rate can include operating the continuous blood flow pump at a first operating speed, and controlling can include operating the continuous blood flow pump at a second operating speed, the second operating speed being associated with a third blood flow rate, the third blood flow rate being greater than the second blood flow rate. Operating the continuous flow blood pump to produce the second blood flow rate includes operating the continuous flow blood pump to produce the second blood flow rate such that the relatively high pressure portion has a duration that is longer than a duration of the relatively low pressure portion. Repeating a cycle in which the duration of the relatively high pressure portion is greater than half of the duration of the cycle. The cycle includes operating the continuous flow blood pump to produce the first blood flow rate, operating the continuous flow blood pump to produce the second blood flow rate, and controlling the continuous flow blood pump to increase the blood flow rate. Operating the continuous flow blood pump to produce the second blood flow rate includes operating the continuous flow blood pump to produce the second blood flow rate such that the second blood flow rate has a predefined relationship with an average blood flow rate of the pulsatile blood flow. The second blood flow rate is substantially equal to an average blood flow rate of the pulsatile blood flow. Controlling the continuous flow blood pump to increase the blood flow rate includes controlling the continuous flow blood pump to increase the blood flow rate through the continuous flow blood pump from the first flow rate to the second flow rate such that the blood flow rate through the continuous flow blood pump overshoots the second flow rate to produce the rate of pressure change that mimics the rate of pressure change of the natural physiologic pulse.

The details of one or more implementations are set forth in the accompanying drawings and the description below. Other features will be apparent from the description and drawings, and from the claims.

DETAILED DESCRIPTION

Figure 1:
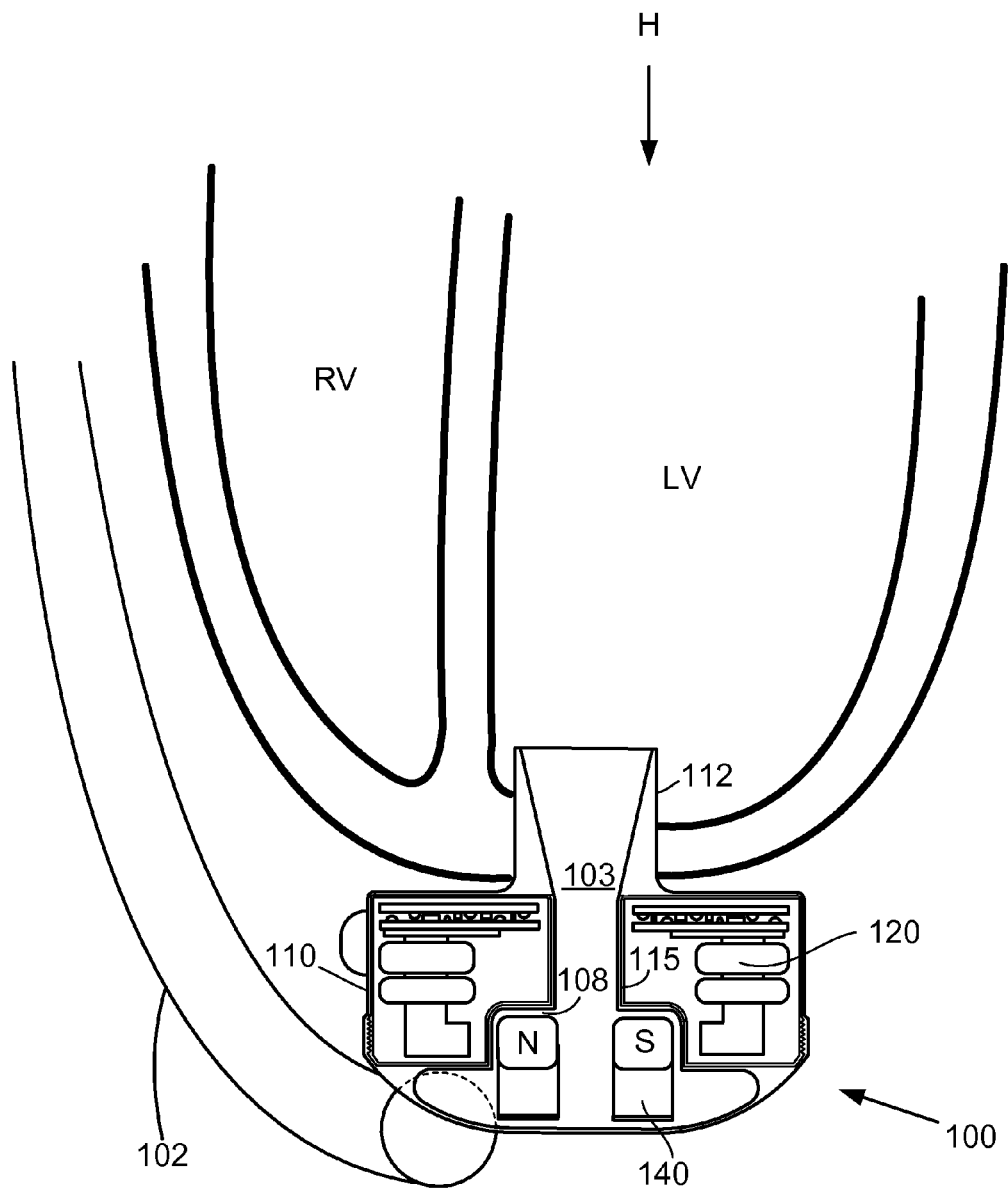
FIG. 1 is a diagram of an implanted blood pump.

With reference to FIG. 1, a left ventricular assist blood pump 100 is implanted in a patient's body to assist or replace the patient's heart H in pumping blood. Pump 100 has a housing 110 including an inlet cannula 112 that extends into the left ventricle LV of the heart H. Connected to the housing 110 is an outlet conduit 102 that conducts blood from the blood pump 100 to the patient's circulatory system. The blood pump 100 can be a continuous flow pump, for example, a rotary pump. The blood pump 100 can provide axial flow, centrifugal flow, or mixed axial and centrifugal flow.

The blood pump 100 includes a stator 120 and a rotor 140. The rotor 140 includes an impeller to move blood from the inlet cannula 112 to the outlet conduit 102. For example, the blood pump 100 can be the pump described in U.S. Provisional Patent Application Ser. No. 61/375,504, filed Aug. 20, 2010, the entire contents of which are hereby incorporated by reference. In some implementations, the rotor 140 is separated from an internal wall 115 of the housing 110 by a gap 108. In use, the gap is from approximately 0.1 millimeters to approximately 2.0 millimeters. For example, in some implementations, the gap 108 is approximately 0.5 millimeters during use. Additionally, in some implementations, the rotor has a weight from approximately 5 grams to approximately 50 grams. For example, in some implementations, the rotor 140 has a weight of approximately 10 grams.

The rotation speed of the rotor 140 can be controlled to produce a desired blood flow rate. The desired blood flow rate can be selected to provide a desired level of assistance to the patient's heart H. For example, the blood flow rate can be selected to partially assist the blood circulation function of the patient's heart H. Alternatively, the blood flow rate can be selected to substantially replace the blood circulation function of the patient's heart. The rate of flow of blood from the inlet cannula 112 to the outlet conduit 102 is controlled, at least in part, by controlling the rate of rotation of the rotor 140 based on a direct relationship between the pump speed and the rate of blood flow through the blood pump 100.

In addition to producing blood flow at a desired rate, a pulsatile blood flow pattern may be desired. A pulsatile blood flow pattern includes time periods of relatively high blood flow rates and blood pressures and time periods of relatively low blood flow rates and blood pressures. Such a pulsatile blood flow pattern may be desired to augment or replace a weakened pulse in patients, especially those whose native cardiac output is small compared to the volume flow rate of the blood pump. Additionally, a pulsatile blood flow pattern may be desired to produce a physiologic response similar to that of a native pulsatile blood flow pattern and/or blood pulse pressure from a healthy heart. This physiologic response may be markedly different than the response of a blood pump operating at a constant speed. While non-pulsatile circulation can lead to certain physiologic, metabolic, and vasomotor changes, the clinical relevance of pulsatility for VADs is unclear. Nevertheless, it is hypothesized that pulsatile circulation may reduce blood stasis in the ventricles, help exercise the aortic valve, improve washing on the distal side of atherosclerotic lesions, increase coronary and/or end organ perfusion, reduce the risk of ventricular suction, reduce the propensity for maladies related to reduced pulsatility, such as arteriovenous malformations, and increase myocardial recovery. Further, it is expected that these phenomena do not require mimicking a native pulse waveform in its entirety. Rather, such may be accomplished with the techniques and waveforms described herein.

Importantly, various characteristics of the artificial pulse may differ substantially from those of a physiologic pulse even while producing a response in the body that is similar to that caused by the physiologic pulse. Although with the multitude of potential clinical advantages there may be different aspects of a native pulse that mediate physiologic response, it is generally understood that the dominant source of dissipated energy that characterizes a meaningful pulse is the pressure wave generated at the start of cardiac systole. Accordingly, the artificial pulse described herein can include a relatively brief perturbation of a nature designed to produce such dissipated energy.

In some implementations, an artificial pulse cycle includes a perturbation period that simulates the pulse pressure that occurs at the leading edge of systole of a physiologic pulse. The perturbation period can include, for example, a period during which the blood pump 100 is operated at a low speed, followed immediately by a period during which the blood pump 100 is operated at a higher speed. The artificial pulse cycle can also include a period longer than the perturbation period during which the pump 100 is operated at an intermediate speed, for example, a speed maintained between the speeds realized during the perturbation period.

Operating the pump at the intermediate speed can contribute to a high operating efficiency. The efficiency achieved can be greater than, for example, the efficiency of a pump that only alternates between equal periods of operation at a high speed and at a low speed. Typically, a continuous flow pump operates with highest efficiency near the middle of its rotational speed range. Therefore, it can be advantageous to operate such a pump at or near a mid-range speed for at least a portion of an artificial pulse cycle.

Some of the parameters that affect physiologic phenomena include pulse pressure and the rate of blood pressure change (dp/dt). For the blood pump 100, for example, pulse pressure and time variation in blood pressure are affected by the angular velocity of the rotor 140. Thus, the blood pump 100 can be selectively controlled to produce a pulsatile blood flow pattern, including a desired pulse pressure and/or a desired rate of pressure change, by producing a pump speed pattern that includes a time period of relatively high rotor rotation speeds and a time period of relatively low rotor rotation speeds. In some implementations, the pulse pressure produced by the blood pump 100 or produced by the blood pump 100 and the patient's heart H in combination can be approximately 10 mmHg or more, such as from approximately 20 mmHg to approximately 40 mmHg.

Figure 2:
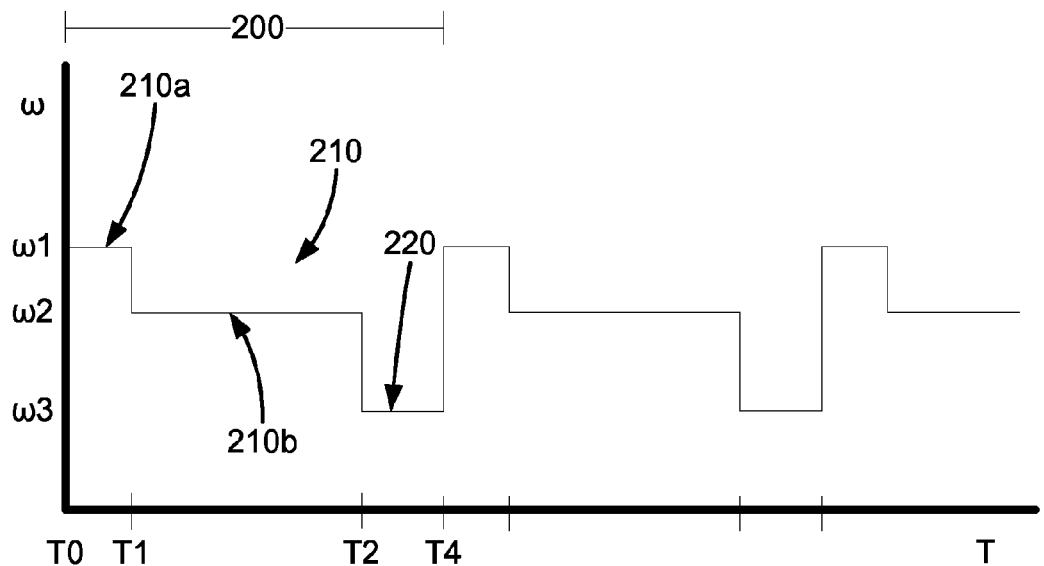
FIGS. 2-5 are diagrams illustrating pump speed patterns.

For example, the blood pump 100 can be operated to produce a pump speed pattern 200, illustrated in FIG. 2. The pump speed pattern 200 includes a first portion 210 with high pump speed producing a relatively high blood pressure, and a second portion 220 with low pump speed producing a relatively low blood pressure. Additionally, the pulsatile blood flow pattern can include a transition between the first portion 210 and the second portion 220 that produces a desired rate of pressure change in the patient's circulatory system, such as a rate of pressure change that simulates a natural physiologic pulse and that produces desired physiological effects associated with rate of pressure change. In some implementations, the rate of pressure change produced by the transition is, for example, between 500 to 1000 mmHg per second.

The first portion 210 and/or the second portion 220 of the pump speed pattern 200 can include multiple segments. In some implementations, the segments each have predetermined durations. As also shown in FIG. 2, the first high speed portion 210 of the pump speed pattern 200 includes a first segment 210a and a second segment 210b. In the first segment 210a, the rotor 140 is rotated at a first rotation speed $\omega 1$ for a first period of time from a time T0 to a time T1. At the time T1, the rotation speed of the rotor 140 is rapidly decreased from the first rotation speed $\omega 1$ a second rotation speed $\omega 2$, producing a stepped transition. The rotor 140 is rotated at the second rotation speed $\omega 2$ for a second period of time from the time T1 to a time T2 during a second segment 210b of the first portion 210 of the pump speed pattern 200. At the time T2, the rotation speed of the rotor 140 is decreased to a third rotation speed $\omega 3$ for a third period of time from the time T2 to a time T4 during the second portion 220 of the pump speed pattern 200. This speed decrease may be as rapid as the aforementioned speed increase, or more gradual to mimic pressure changes during native diastole.

In the pump speed pattern 200, the second rotation speed $\omega 2$ is a target high blood flow pump speed, and the first rotation speed $\omega 1$ is a desired overshoot pump speed that is selected to increase the rate of change of the blood pressure during the first period. The first period of time from the time T0 to the time T1, during which the blood pump 100 is operated at the first rotation speed $\omega 1$, is shorter than the second period of time from the time T1 to the time T2, during which the blood pump 100 is operated at the second rotation speed $\omega 2$. The first period of time can be from approximately 0.01 seconds to approximately 1 second. In some implementations, the first period of time is approximately 0.05 seconds in duration. In some implementations, the first period of time can be approximately equal to, or greater than the second period of time.

Additionally, the duration of the first period can be selected to produce a desired pulse pressure, i.e., the difference between blood pressure before the speed change time T1 and during the time T1, and can be selected independently of the duration of the second period of time. The first portion 210, including the first and second time periods from the time T0 to the time T2, is longer than the second portion 220. In some implementations, the first and second time periods from the time T0 to the time T2 can be shorter than, longer than, or substantially the same duration as the second portion 220. For example, to increase the duration of pumping at the higher flow rate relative to pumping at the lower rate while still benefiting from the occasional pulse, it may be advantageous for the first portion 210 to be longer than the second portion 220. If desired, the speed of the blood pump 100 is increased to the first rotation speed $\omega 1$ and the pump speed pattern 200 can be repeated. The pump speed pattern 200 can be repeated on a continuous or discontinuous basis, and the increase of rotation speed of the rotor 140 is also sufficiently rapid to produce a desired rate of pressure change.

The concept of overshooting the rotation speed $\omega 2$ with a greater speed, such as rotation speed $\omega 1$, is based upon partly decoupling pulse pressure, i.e. the difference between the blood pressures before and after the speed change, from the volume flow rate at the higher speed. Thus, target pulse pressures and volume flow rates can be attained at various flow conditions. Ideal values will vary with particular pump design and requirements.

As shown in FIG. 2, the period 210b can be longer than the period 210a. The period 210b can also be longer than the portion 220. In some implementations, the duration of the period 210b is more than half of the duration of the pump speed pattern 200. For example, the duration of the period 210b can be 60%, 70%, 80% or more of the duration of the pump speed pattern 200. As an alternative, depending on patient needs and pump characteristics, the duration of the period 210b can be 50% or less of the duration of the pump speed pattern 200, for example, 40%, 30%, 20% or less.

Operating the pump at the rotation speed $\omega 2$ during the period 210b can contribute to a high hydraulic efficiency during the pump speed pattern 200. During the pump speed pattern 200, the pulse pressure generated in a patient's body is generally correlated to the change in pump rotation speed, for example, the magnitude of the speed change between the speeds $\omega 3$ and $\omega 1$ at time T4. Therefore, to simulate a pressure change that occurs at the beginning of systole of a physiologic pulse, a significant speed differential between the rotation speeds $\omega 3$ and $\omega 1$ is generally desired. The speed differential can be, for example, 1000 rpm, 2000 rpm, or more depending on the characteristics of the blood pump 100. Due to the magnitude of the speed differential, one or both of the speeds $\omega 3$ to $\omega 1$ may occur outside the range of highest operating efficiency of the blood pump 100.

The rotation speed $\omega 2$ can be a speed that results in a high hydraulic efficiency of the blood pump 100, for example, a speed near the middle of the operating range of the blood pump 100. During the pump speed pattern 200, the blood pump 100 can operate at the speed $\omega 2$ that results in high efficiency for a significant portion of the pump speed pattern 200, contributing to a high efficiency. As described above, the blood pump 100 can operate at the speed $\omega 2$ for more than half of the duration at the pump speed pattern 200. Thus the blood pump 100 can operate in a highly efficient manner for the majority of the pump speed pattern 200 and can also produce a pressure change that simulates the beginning of systole of a physiologic heart. Accordingly, some implementations of the pump speed pattern 200 can provide a higher efficiency than control modes that attempt to mimic all aspects of a native cardiac cycle.

The length of the period 210b relative to the length of the pump speed pattern 200 can vary based on the frequency of the artificial pulse. The duration of the period 210a and of the portion 220, by contrast, can be independent of the pulse rate. To produce the desired physiological response, a minimum duration for the period 210a and the portion 220 can be selected, for example, 0.125 seconds. The period 210b can fill the remainder of the pump speed pattern 200.

As an example, the pump speed pattern 200 can have a duration of one second, for a frequency of 60 cycles per minute. Given that the period 210a and the portion 220 have a combined duration of 0.125 seconds, the period 210b can have a duration of 0.750 seconds, or 75% of the pump speed pattern 200. As another example, when the pump speed pattern 200 has a duration of two seconds (and thus a frequency of 30 cycles per minute), the duration of the period 210b can be 1.75 seconds, which is 87.5% of the duration of the pump speed pattern 200.

In some implementations, the rotation speed $\omega 2$ is selected such that the operation of the blood pump 100 at the rotation speed $\omega 2$ produces a flow rate that has a predetermined relationship relative to the average flow rate during the pump speed pattern 200. The flow rate during the portion 210b can be within a predefined range of the average flow rate, for example, within 30% or within 10% of the average flow rate. The flow rate during the portion 210b can be substantially equal to the average flow rate.

Selecting the rotation speed $\omega 2$ to produce a flow rate that is substantially equal to the average flow rate can facilitate a transition between a pulsatile control mode and another control mode, such as a continuous flow control mode. In some implementations, the blood pump 100 operates at a particular constant speed for the greater part of the pump speed pattern 200. Operation at the constant speed can occur during, for example, the period 210b. By adjusting the speeds $\omega 1$ and $\omega 3$ and duration of the period 210a and of the portion 220, the average pump volume flow rate can be tuned to substantially match an average pump volume flow rate that would be realized in a different optional setting. Consequently, a clinician or patient can switch from an artificial pulse mode to another control mode in a manner that causes only a small difference or no difference in average volume flow rate. This can provide a clinical advantage when the artificial pulse is a selectable option among at least one alternative, for example, a constant speed option.

As an example, a speed set by a clinician for a constant speed mode can also be utilized for a constant speed portion of an artificial pulse mode. The speed can be selected by the clinician to produce a desired volume flow rate through the blood pump 100 during the constant speed mode (e.g., during continuous flow or non-pulsatile operation of the blood pump 100). In the artificial pulse mode, the same selected speed can be used as, for example, the rotation speed $\omega 2$ during the period 210b of the pump speed pattern 200. The speeds $\omega 1$, $\omega 3$ and the duration of the period 210a and the portion 220 are calculated or chosen to approximately balance the volume flow rate for the pump speed pattern 200. For example, the reduced flow rate during the portion 220 can offset the increased flow rate during the portion 210a. As a result, the net volume flow rate during the pump speed pattern 200 can substantially match the volume flow rate during the constant speed mode. Thus in either the constant speed mode or the artificial pulse mode, the volume flow rate can be approximately the same, permitting the clinician to switch from one mode to another without affecting the volume flow rate. This can help avoid potentially dangerous conditions that could occur if switching from one mode to another resulted in sudden changes in flow rate. For example, a sudden decrease in volume flow rate could cause acutely insufficient perfusion for the patient, and a sudden increase in volume flow rate could cause ventricular suction and arrhythmia.

Figure 3:
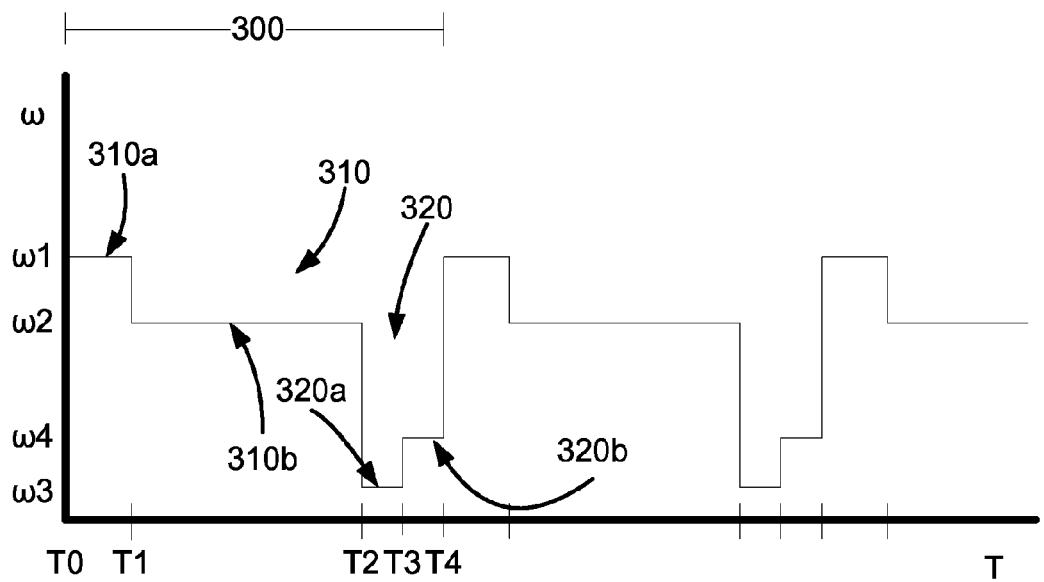

As mentioned above, the second portion 210 of the pump speed pattern 200 can also include multiple segments. For example, as shown in FIG. 3, a pump speed pattern 300 includes a first portion 310 that has a first segment 310a and a second segment 310b and the pump speed pattern 300 includes a second portion 320 that has a first segment 320a and a second segment 320b. During the first segment 310a, from the time T0 to the time T1, the blood pump 100 is operated at the first rotation speed $\omega 1$. At the time T1, the speed of the blood pump 100 is reduced to the second rotation speed $\omega 2$, and the blood pump 100 is operated at the second rotation speed $\omega 2$ for the second period of time from the time T1 to the time T2. At the time T2, the speed of the blood pump 100 is reduced from the second speed $\omega 2$ to the third rotation speed $\omega 3$. The blood pump 100 is operated at the third rotation speed $\omega 3$ for a third period of time from the time T2 to a time T3 during a first segment 320a of the second portion 320 of the pump speed pattern 300. At the time T3, the speed of the blood pump 100 is increased from the third rotation speed ω3 to a fourth rotation speed ω4, and the blood pump 100 is operated at the fourth rotation speed ω4 during a fourth period of time from the time T3 to the time T4 during a second segment 320b of the second portion 320 of the pump speed pattern 300. If desired, the speed of the blood pump 100 is increased to the first rotation speed ω1 and the pump speed pattern 300 can be repeated. The pump speed pattern 300 can be repeated on a continuous or discontinuous basis, and the increase of rotation speed of the rotor 140 is also sufficiently rapid to produce a desired rate of pressure change.

Similar to the concept of overshooting ω2 in pattern 200, the concept of overshooting the rotation speed ω4 with a lower rotation speed, such as the rotation speed ω3, is also based upon decoupling pulse pressure from the volume flow rate at the lower rotation speed ω4. Thus, the pump speed pattern 300 more completely decouples target pulse pressures and volume flow rates than the pump speed pattern 200, and ideal values can be attained, or more closely approximated, at various flow conditions.

Figure 4:
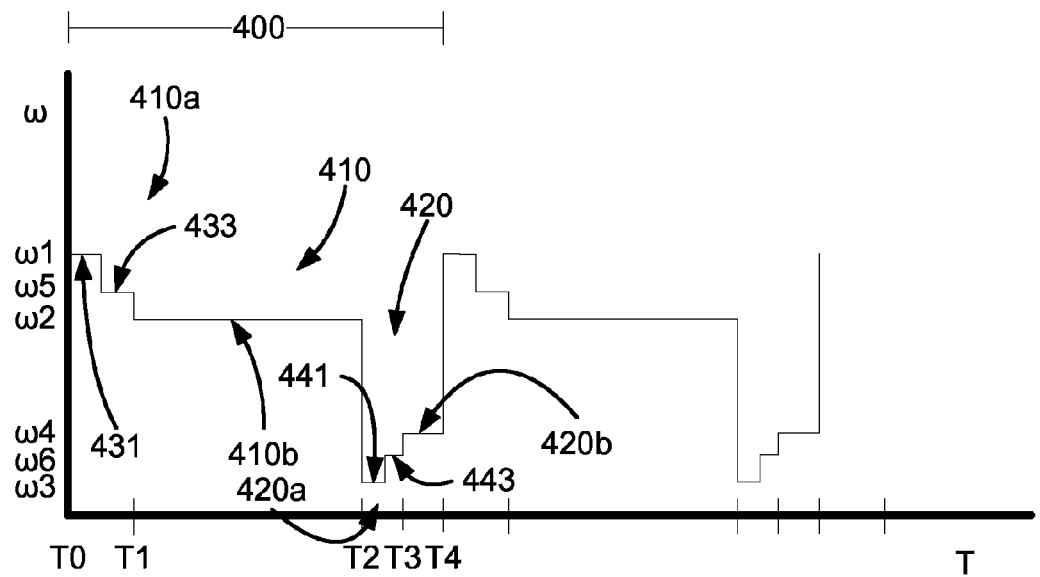

While a single overshoot pump speed for a transition between pump speeds are illustrated and described with reference to FIGS. 2 and 3, multiple overshoot pump speeds for one or more transitions can be used. For example, FIG. 4 illustrates a pump speed pattern 400 that includes multiple overshoot pump speeds for each transition. The pump speed pattern 400 includes a first portion 410 having a first segment 410a and a second segment 410b, and that includes a second portion 420 having a first segment 420a and a second segment 420b. The first segment 410a of the first portion 410 of the pump speed pattern 400 includes a first step 431 during which the blood pump 100 is operated at the first rotation speed ω1 to overshoot the target pump speed ω2 and a second transition step 433 during which time the blood pump 100 is operated at a fifth speed ω5 to transition from the first rotation speed ω1 to the second rotation speed ω2. Similarly, the first segment 420a of the second portion 420 includes a first step 441 during which the blood pump 100 is operated at the third rotation speed ω3 and a second segment 443 during which the blood pump 100 is operated at a sixth speed ω6 to transition between the third speed ω3 and the fourth rotation speed ω4. If desired, the speed of the blood pump 100 is increased to the first rotation speed ω1 and the pump speed pattern 400 can be repeated. The pump speed pattern 400 can be repeated on a continuous or discontinuous basis, and the increase of rotation speed of the rotor 140 is also sufficiently rapid to produce a desired rate of pressure change.

The concept of creating multiple stepwise rotation speed changes is based upon producing the physiologic response that is similar to that produced during human cardiac systole and diastole. This is distinct from mimicking the nature of a native pulse waveform in its entirety. As described above, greater hydraulic efficiency can often be achieved by avoiding imitation of the physiologic pressure waveform over the pulse cycle. It was previously mentioned that an artificial pulse offers a multitude of potential clinical advantages. For some or all of these potential clinical advantages, the benefit of closely matching the energy dissipated during a healthy native pulse varies. To the extent that close matching facilitates achieving these potential clinical advantages, the additional complexity of pattern 400 may be warranted.

In contrast to the stepped or discontinuous transitions discussed above with respect to FIGS. 2-4, smooth or continuous transitions may be used in place of, or in combination with, stepped transitions between different pump operation speeds.

Figure 5:
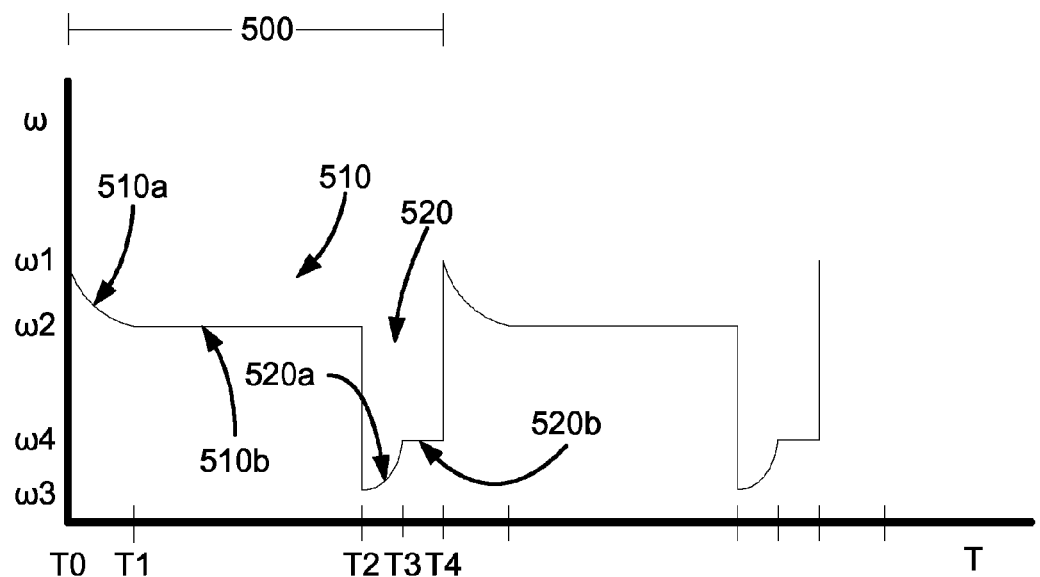

For example, smooth transitions are illustrated in the pump speed pattern 500 of FIG. 5. The pump speed pattern 500 includes a first portion 510 and a second portion 520. The first portion 510 includes a first segment 510a during which the speed of the pump 100 is decreased gradually, at a strategically-selected rate, from the first rotation speed ω1 to the second rotation speed ω2 from the time T0 to the time T1. The selected rate of pump speed decrease can be, for example, a particular linear rate or a particular non-linear rate. During the second segment 510b of the first portion 510, from the time T2 to the time T2, the blood pump 100 is operated at the second rotation speed ω2. Similarly, the second portion 520 includes a first segment 520a during which the speed of the blood pump 100 is increased gradually, at a strategically-selected rate, from the third rotation speed ω3 to the fourth rotation speed ω4 from the time T2 to the time T3. During the second segment 520b of the second portion 520, from the time T3 to the time T4, the blood pump 100 is operated at the fourth rotation speed ω4. If desired, at time T4, there is a step increase in the rotation speed of the rotor 140 can be rapidly increased to the first rotation speed ω1, and the pump speed pattern 500 is repeated.

The concept of creating multiple speed changes at a strategically-selected rate is based upon producing the physiologic response that is similar to that produced during human cardiac systole and diastole. For example, if very accurate matching of energy dissipation during a human pulse is necessary, the additional complexity of pattern 500 may be warranted.

The pump speed pattern 500 illustrates the difference between stepped transitions discussed above with respect to pump speed patterns 200-400, produced by rapidly changing the rotation speed of the rotor 140, and the gradual transitions of the first segment 510a of the first portion 510 and the first segment 520a of the second portion 520 of the pump speed pattern 500. Such gradual transitions can be included, for example, to mimic pressure changes exhibited during native diastole, as may be achieved by the gradual transition of the first segment 510a of the first portion 510 of the pump speed pattern 500. In some implementations, one or more of the rotation speed decreases of a pump speed pattern can be gradual transitions. For example, a pump speed pattern can include a gradual decrease in rotation speed from the first rotation speed ω1 to the third rotation speed ω3 and a stepped transition from the third pump speed ω3 back to the first rotation speed ω1. Various combinations of stepped and gradual transitions can be included in a pump speed pattern to produce a desired arterial pressure wave form, or other desired physiologic effect. Additionally, the type of transition between rotation speeds can affect power consumption of the blood pump 100, and the pump speed pattern can be selected based, at least in part, on power consumption considerations.

For all the pump speed patterns discussed it should be appreciated that although rotor speed is the technological parameter utilized to impart an artificial pulse, any physiologic effect is related to the consequential pressure and flow patterns, including pulse pressure, the maximum time variation in rate of blood pressure change (dp/dt), and the like. Rotor speed is not intrinsically physiologically meaningful. The human vascular system naturally dampens the native pulse produced by the heart, and it will do the same for an artificial pulse produced as described. The invention describes a utilitarian combination of factors that result in a physiological meaningful pulse. Thus, the pump speed patterns 200-500 described above are exemplary combinations of parameters that result in a physiologically meaningful pulse.

Figure 6:
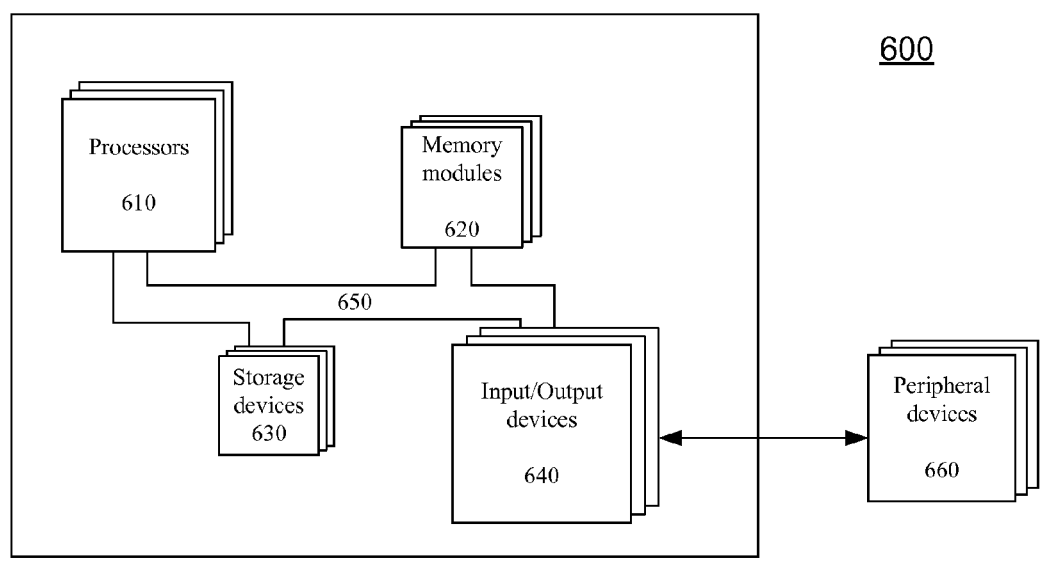
FIG. 6 is a diagram of a computer system.

In use, the pump speed patterns 200-500 can be generated by a controller that is configured to generate an electrical drive signal to operate the blood pump 100. For example, the controller can include a computer system 600, shown in FIG. 6, that outputs an electrical current to operate the blood pump 100. In order to produce the pump speed pattern 200 described above, the controller outputs a first electrical current from the time T0 to the time T1. At the time T1, the controller reduces the output electrical current to a second current that is lower than the first electrical current, and outputs the second electrical current from the time T1 to the time T2. At the time T2, the controller reduces the output electrical current from the second current to a third current, and outputs the third electrical current from the time T2 to the time T4.

The computer system 600 includes one or more processors 610, memory modules 620, storage devices 630, and input/output devices 640 connected by a system bus 650. The input/output devices 640 are operable to communicate signals to, and/or receive signals from, one or more peripheral devices 660. For example, a peripheral device 660 can be used to store computer executable instructions on the memory modules 620 and/or the storage devices 630 that are operable, when executed by the processors, to cause the controller to generate a waveform to control the operation of the pump 100 and produce a pump speed pattern, such as the pump speed patterns 200-500.

Additionally, the controller can include a sensor that provides a signal that indicates activity of the heart H. For example, the controller can include a sensor that provides a signal indicative of power consumption of the blood pump 100. The signal can be used to determine when the left ventricle LV contracts. For example, the power consumption of the blood pump 100 may, for a given operating speed, increase as the left ventricle LV contracts. Based on the determined heart activity, the controller can adjust the generated control waveform. For example, the controller can automatically adjust the timing and duration of the first portion 210 and the second portion 220 of the pump speed pattern 200 such that the first portion 210 approximately coincides with a contraction of the left ventricle LV. The pump 100 is controlled such that the time T0 approximately coincides with a beginning of a contraction of the left ventricle LV and the time T2 approximately coincides with an end of the contraction of the left ventricle LV. The time T4 approximately coincides with a beginning of a subsequent contraction of the left ventricle LV. Thus, the durations of the various portions and/or segments of the pump speed patterns described above can be changed individually or collectively for one or more repetitions of the pump speed patterns. Using these techniques, the controller can synchronize the pulsatile operation of the blood pump 100 with the natural physiologic pulse of the heart H.

Alternatively, the controller can generate the control waveform independently of the activity of the heart H and/or to operate in opposition to the activity of the heart H, such as where the first portion 210 occurs during left ventricular relaxation. Similarly, the controller can generate a control waveform that includes a distinctly non-physiologic pulse rate, such as fewer than 40 high-pressure periods per minute, and the waveform can be generated independently of native heart function. In some examples, the blood pump 100 can be operated to produce distinctly physiologic pulse rates, such as between 50 and 110 high-pressure periods per minute, and can be controlled dependently or independently of heart function.

A number of implementations have been described. Nevertheless, it will be understood that various modifications may be made without departing from the spirit and scope of the claimed invention. For example, the pump speed patterns described above can be used with various types of blood pumps, including axial flow blood pumps and centrifugal flow blood pumps. Similarly, the rotors of blood pumps used to produce pulsatile blood flow patterns as described above may be electromagnetically-suspended, hydraulically-suspended, mechanically-suspended, or combinations thereof. The rotors may also partially be passively magnetically-suspended. However, the effect of an artificial pulse may most accurately be simulated by a pump in which the rotor is electromagnetically suspended, with or without partial passive magnetic suspension, because in general, other things being equal, electromagnetic suspension yields a high degree of responsiveness of the rotor to speed change inputs. For example, mechanical bearings associated with mechanical suspension and/or very narrow rotor clearance gaps associated with hydraulic suspension hinder rapid acceleration of the rotor compared to similar pumps that employ electromagnetic suspension. Additionally, while the pump speed patterns described above have been described with regard to a measure of angular velocity, the pump speed patterns can be produced with regard to one or more different measures of pump speeds. Additionally, there may be a delay between a change in drive signal generated by the controller and a change in operating speed of the blood pump. Thus, the controller can be operated such that changes in the output drive signal are effected at a time to produce a corresponding change in pump operating speed at a desired time, such as a time that approximately coincides with selected activity of the heart.

In some implementations, the pump speed patterns 200-500 can include additional portions or segments during which the blood pump is operated at other speeds. For example, at desired times, the blood pump can be operated to produce a pump speed pattern that produces a desired physiologic effect, such as opening or closing the aortic valve. Such operation of the blood pump can interrupt a generally continuous repetition of a selected one or more of the pump speed patterns described above, or others, including an indefinite period of constant speed, and a selected pump speed pattern can be resumed after the desired physiologic effect has been produced. The pump speed patterns 200-500 can also include different portions or segments. For example, the second segment 210b of the first portion 210 of the pump speed pattern 200 can include multiple pump speeds. Similarly, the transitions between pump speeds, such as the reduction in pump speed from the first rotation speed $\omega 1$ to the second rotation speed $\omega 2$, can include constant, variable, exponential, combinations thereof, or other rate of speed change over time such that the transition, such as the first segment 510a of the first portion 510 of the pump speed pattern 500, is linear, curvilinear, parabolic, logarithmic, sinusoidal, stepped, or combinations thereof.

In some implementations, one or more of the pump speed changes in the pump speed patterns 200-500 can be monotonic. A transition from one speed to another may occur gradually over a period of time, yet change directly from one speed to another. For example, to decrease a pump speed from a first rotational speed to a second rotational speed, the controller can reduce the pump speed without causing an intervening period of increasing pump speed. Similarly, the transition from the first rotational speed to the second rotational speed can occur without operating the pump above the first rotational speed during the transition.

Additionally, a blood pump can be operated according to a pump speed pattern that is selected according to a pump power consumption rate associated with the pump speed pattern, a pump efficiency associated with the pump speed pattern, a blood flow rate associated with the pump speed pattern, and/or a rate of blood pressure change associated with the pump speed pattern. For example, in a first mode, the controller can be operated to produce a pump speed pattern that produces a desired rate of blood pressure change. When a low power condition is detected, the controller can be switched to a power-saving mode to produce a pump speed pattern that has a low power consumption rate, even if the desired rate of pressure change is not produced in the power-saving mode.

As mentioned above, in some implementations, the blood pump 100 can be used to assist a patient's heart during a transition period, such as during a recovery from illness and/or surgery or other treatment. In other implementations, the blood pump 100 can be used to partially or completely replace the function of the patient's heart on a generally permanent basis, such as where the patient's aortic valve is surgically sealed.

The subject matter and the functional operations described in this specification can be implemented in digital electronic circuitry, in tangibly-embodied computer software or firmware, in computer hardware, including the structures disclosed in this specification and their structural equivalents, or in combinations of one or more of them. The subject matter described in this specification can be implemented as one or more computer programs, i.e., one or more modules of computer program instructions encoded on a tangible non transitory program carrier for execution by, or to control the operation of, data processing apparatus. The program carrier can be a computer storage medium, for example, a machine-readable storage device, a machine-readable storage substrate, a random or serial access memory device, or a combination of one or more of them, as described further below. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read only memory or a random access memory or both. The essential elements of a computer are a processing unit for performing or executing instructions and one or more memory devices for storing instructions and data. A computer can also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a pump, a pump controller, or a portable storage device, e.g., a universal serial bus (USB) flash drive or other removable storage module, to name a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Accordingly, other embodiments are within the scope of the following claims.

The invention claimed is:

1. A method for producing a pulsatile blood flow having a relatively low pressure time period portion and a relatively high pressure time period portion and having a temporal rate of pressure change that mimics a temporal rate of pressure change of a natural physiologic pulse, the method comprising:
   repeating a cycle in which the duration of the relatively high pressure time period portion is greater than half of the duration of the cycle, the cycle comprising:
      operating a continuous flow blood pump to produce a first blood flow rate through the continuous flow blood pump associated with the relatively low pressure time period portion of the pulsatile blood flow;
      operating the continuous flow blood pump to produce a second blood flow rate through the continuous flow blood pump associated with the relatively high pressure time period portion of the pulsatile blood flow; and
      controlling the continuous flow blood pump to increase a blood flow rate through the continuous flow blood pump from the first flow rate to the second flow rate to produce the temporal rate of pressure change that mimics the temporal rate of pressure change of the natural physiologic pulse.

2. The method of claim 1, wherein:
   operating the continuous blood flow pump to produce the second blood flow rate comprises operating the continuous blood flow pump at a first operating speed; and controlling comprises operating the continuous blood flow pump at a second operating speed, the second operating speed being associated with a third blood flow rate, the third blood flow rate being greater than the second blood flow rate.

3. The method of claim 1, wherein the cycle further comprises controlling the continuous flow blood pump to decrease a blood flow rate through the pump from the second flow rate to the first flow rate.

4. The method of claim 1, further comprising:
controlling the continuous flow blood pump to decrease a blood flow rate through the pump from the second flow rate to a third flow rate, the third blood flow rate being less than the second blood flow rate; and
controlling the continuous flow blood pump to increase a blood flow rate through the pump from the third blood flow rate to the first blood flow rate.

5. The method of claim 1, wherein controlling the continuous flow blood pump to increase a blood flow rate through the continuous flow blood pump comprises controlling the continuous flow blood pump to increase a speed of the continuous blood pump with a step-wise transition from a speed that produces the first blood flow rate to a speed that produces the second blood flow rate.

6. The method of claim 1, wherein controlling the continuous flow blood pump to increase a blood flow rate through the continuous flow blood pump comprises controlling the continuous flow blood pump to increase a speed of the continuous blood pump with a linear transition from a speed that produces the first blood flow rate to a speed that produces the second blood flow rate.

7. The method of claim 1, wherein controlling the continuous flow blood pump to increase a blood flow rate through the continuous flow blood pump comprises controlling the continuous flow blood pump to increase a speed of the continuous blood pump with a curvilinear transition from a speed that produces the first blood flow rate to a speed that produces the second blood flow rate.

8. The method of claim 1, further comprising synchronizing, based on a relationship between a speed of the continuous flow blood pump and a power consumption of the continuous flow blood pump, operation of the continuous flow blood pump and contraction of a ventricle of a human heart that is in blood flow communication with the blood pump.

9. The method of claim 1, wherein controlling the continuous flow blood pump to increase a blood flow rate through the continuous flow blood pump from the first flow rate to the second flow rate comprises controlling the continuous flow blood pump to increase the speed of the blood pump at a beginning of a contraction of a ventricle of a human heart that is in blood flow communication with the blood pump.

10. The method of claim 9, further comprising reducing the speed of the blood pump at an ending of the contraction of the ventricle of the human heart.

11. The method of claim 1, further comprising selecting the first flow rate and the second flow rate to produce a desired average blood flow rate of the pulsatile blood flow.

12. The method of claim 1, further comprising switching between operating the continuous flow blood pump to produce the pulsatile blood flow and operating the continuous flow blood pump to produce a non-pulsatile flow.

13. The method of claim 1, further comprising switching between operating the continuous flow blood pump to produce the pulsatile blood flow and operating the continuous flow blood pump at a substantially constant speed.

14. The method of claim 1, wherein the duration of the cycle is between about 0.01 second and about 1 second.

15. The method of claim 1, further comprising operating the pump for another cycle, wherein the second blood flow rate is reduced during the another cycle relative to the cycle.

16. The method of claim 1, wherein controlling the continuous flow blood pump to increase a blood flow rate through the continuous flow blood pump from the first flow rate to the second flow rate comprises controlling the continuous flow blood pump to increase a speed of the blood pump to cause a pulse pressure of approximately 10 mmHg or more.

17. A method for producing a pulsatile blood flow having a relatively low pressure time period portion and a relatively high pressure time period portion and having a temporal rate of pressure change that mimics a temporal rate of pressure change of a natural physiologic pulse, the method comprising:
operating a continuous flow blood pump to produce a first blood flow rate through the continuous flow blood pump associated with the relatively low pressure time period portion of the pulsatile blood flow;
operating the continuous flow blood pump to produce a second blood flow rate through the continuous flow blood pump associated with the relatively high pressure time period portion of the pulsatile blood flow, the second blood flow rate being substantially equal to an average blood flow rate of the pulsatile blood flow; and
controlling the continuous flow blood pump to increase a blood flow rate through the continuous flow blood pump from the first flow rate to the second flow rate to produce the temporal rate of pressure change that mimics the temporal rate of pressure change of the natural physiologic pulse.

18. The method of claim 17, further comprising repeating a cycle that comprises:
operating the continuous flow blood pump to produce the first blood flow rate through the continuous flow blood pump;
operating the continuous flow blood pump to produce the second blood flow rate through the continuous flow blood pump;
controlling the continuous flow blood pump to increase a blood flow rate through the continuous flow blood pump from the first flow rate to the second flow rate to produce the rate of pressure change that mimics the temporal rate of pressure change of the natural physiologic pulse; and
operating the continuous flow blood pump to produce a third blood flow rate through the continuous flow blood pump associated with the relatively high pressure time period portion of the pulsatile blood flow, the third blood flow rate being higher than the second blood flow rate.

19. The method of claim 18, wherein the continuous flow blood pump is operated to produce the first blood flow rate for a first predetermined amount of time, wherein the continuous flow blood pump is operated to produce the second blood flow rate for a second predetermined amount of time; and wherein the continuous flow blood pump is operated to produce the third blood flow rate for a third predetermined amount of time.

20. The method of claim 17, wherein controlling the continuous flow blood pump to increase a blood flow rate through the continuous flow blood pump comprises controlling the continuous flow blood pump to increase a speed of the continuous blood pump with a step-wise transition, linear transition, or a curvilinear transition from a speed that produces the first blood flow rate to a speed that produces the second blood flow rate.

21. The method of claim 17, further comprising synchronizing, based on a relationship between a speed of the continuous flow blood pump and a power consumption of the continuous flow blood pump, operation of the continuous flow blood pump and contraction of a ventricle of a human heart that is in blood flow communication with the blood pump.

22. The method of claim 17, wherein controlling the continuous flow blood pump to increase a blood flow rate through the continuous flow blood pump from the first flow rate to the second flow rate comprises controlling the continuous flow blood pump to increase the speed of the blood pump at a beginning of a contraction of a ventricle of a human heart that is in blood flow communication with the blood pump.

23. The method of claim 22, further comprising reducing the speed of the blood pump at an ending of the contraction of the ventricle of the human heart.

24. The method of claim 17, wherein the continuous flow blood pump is operated to produce the first blood flow rate for a first predetermined amount of time and wherein the continuous flow blood pump is operated to produce the second blood flow rate for a second predetermined amount of time.

25. The method of claim 17, wherein controlling the continuous flow blood pump to increase a blood flow rate through the continuous flow blood pump from the first flow rate to the second flow rate comprises controlling the continuous flow blood pump to increase a speed of the blood pump to cause a pulse pressure of approximately 10 mmHg or more.

26. The method of claim 17, wherein the second flow rate is within a predefined range of an average flow rate.

27. The method of claim 26, wherein the second flow rate is within 30% of the average flow rate.

28. A method for producing a pulsatile blood flow having a relatively low pressure time period portion and a relatively high pressure time period portion and having a temporal rate of pressure change that mimics a rate of pressure change of a natural physiologic pulse, the method comprising:
    operating a continuous flow blood pump to produce a first blood flow rate through the continuous flow blood pump associated with the relatively low pressure time period portion of the pulsatile blood flow;
    operating the continuous flow blood pump to produce a second blood flow rate through the continuous flow blood pump associated with the relatively high pressure time period portion of the pulsatile blood flow; and
    controlling the continuous flow blood pump to increase a blood flow rate through the continuous flow blood pump from the first flow rate to the second flow rate such that the blood flow rate through the continuous flow blood pump overshoots the second flow rate to produce the temporal rate of pressure change that mimics the temporal rate of pressure change of the natural physiologic pulse.

29. The method of claim 20, wherein operating the continuous flow blood pump to produce the second blood flow rate comprises operating the continuous flow blood pump to produce the second blood flow rate such that the relatively high pressure time period portion has a duration that is longer than a duration of the relatively low pressure time period portion.

30. The method of claim 20, wherein operating the continuous flow blood pump to produce the second blood flow rate comprises operating the continuous flow blood pump to produce the second blood flow rate such that the second blood flow rate has a predefined relationship with an average blood flow rate of the pulsatile blood flow.

31. The method of claim 20, further comprising synchronizing, based on a relationship between a speed of the continuous flow blood pump and a power consumption of the continuous flow blood pump, operation of the continuous flow blood pump and contraction of a ventricle of a human heart that is in blood flow communication with the blood pump.

32. The method of claim 20, wherein the continuous flow blood pump is operated to produce the first blood flow rate for a first predetermined amount of time and wherein the continuous flow blood pump is operated to produce the second blood flow rate for a second predetermined amount of time.

33. A method for producing a pulsatile blood flow having a relatively low pressure portion and a relatively high pressure portion and having a rate of pressure change that mimics a rate of pressure change of a natural physiologic pulse, the method comprising:
    repeating a cycle in which the duration of the relatively high pressure portion is greater than half of the duration of the cycle, the cycle comprising:
        operating a continuous flow blood pump to produce a first blood flow rate through the continuous flow blood pump associated with the relatively low pressure portion of the pulsatile blood flow;
        operating the continuous flow blood pump to produce a second blood flow rate through the continuous flow blood pump associated with the relatively high pressure portion of the pulsatile blood flow; and
        controlling the continuous flow blood pump to increase a blood flow rate through the continuous flow blood pump from the first flow rate to the second flow rate to produce the rate of pressure change that mimics the rate of pressure change of the natural physiologic pulse; and
    wherein controlling the continuous flow blood pump to increase a blood flow rate through the continuous flow blood pump from the first flow rate to the second flow rate comprises controlling the continuous flow blood pump to increase a speed of the blood pump to cause a rate of pressure change of between 500 to 1000 mmHg per second.

34. A method for producing a pulsatile blood flow having a relatively low pressure portion and a relatively high pressure portion and having a rate of pressure change that mimics a rate of pressure change of a natural physiologic pulse, the method comprising:
    operating a continuous flow blood pump to produce a first blood flow rate through the continuous flow blood pump associated with the relatively low pressure portion of the pulsatile blood flow;
    operating the continuous flow blood pump to produce a second blood flow rate through the continuous flow blood pump associated with the relatively high pressure portion of the pulsatile blood flow, the second blood flow rate being substantially equal to an average blood flow rate of the pulsatile blood flow; and
    controlling the continuous flow blood pump to increase a blood flow rate through the continuous flow blood pump from the first flow rate to the second flow rate to produce the rate of pressure change that mimics the rate of pressure change of the natural physiologic pulse; and
    wherein controlling the continuous flow blood pump to increase a blood flow rate through the continuous flow blood pump from the first flow rate to the second flow rate comprises controlling the continuous flow blood pump to increase a speed of the blood pump to cause a temporal rate of pressure change of between 500 to 1000 mmHg per second.

35. A method for producing a pulsatile blood flow having a relatively low pressure portion and a relatively high pressure portion and having a rate of pressure change that mimics a rate of pressure change of a natural physiologic pulse, the method comprising:

operating a continuous flow blood pump to produce a first blood flow rate through the continuous flow blood pump associated with the relatively low pressure portion of the pulsatile blood flow;

operating the continuous flow blood pump to produce a second blood flow rate through the continuous flow blood pump associated with the relatively high pressure portion of the pulsatile blood flow; and controlling the continuous flow blood pump to increase a blood flow rate through the continuous flow blood pump from the first flow rate to the second flow rate such that the blood flow rate through the continuous flow blood pump overshoots the second flow rate to produce the rate of pressure change that mimics the rate of pressure change of the natural physiologic pulse; and wherein controlling the continuous flow blood pump to increase a blood flow rate through the continuous flow blood pump from the first flow rate to the second flow rate comprises controlling the continuous flow blood pump to increase a speed of the blood pump to cause a temporal rate of pressure change of between 500 to 1000 mmHg per second.

36. A controller configured to output an electrical current to operate a continuous flow blood pump to produce a pump speed pattern, the pump speed pattern comprising:

a first time period segment for operating the pump at a first rotation speed and a second rotation speed reduced from the first rotation speed; and a second time period segment for operating the pump at a third rotation speed reduced from the second rotation speed and a fourth rotation speed different from the third rotation speed;

wherein the controller is configured to increase a blood flow rate through the pump from the first flow rate to the second flow rate to produce a pulse pressure.

37. The controller of claim 36, wherein the fourth rotation speed is reduced relative to the second rotation speed.

38. The controller of claim 36, wherein the speed pattern comprises a transition from the first rotation to the second rotation speed to cause a pulse pressure of approximately 10 mmHg or more.

\* \* \* \* \*